(12) United States Patent
Perraut et al.

(10) Patent No.: US 10,473,576 B2
(45) Date of Patent: Nov. 12, 2019

(54) SYSTEM FOR ANALYSING A TRANSPARENT SAMPLE WITH CONTROL OF POSITION, AND ASSOCIATED METHOD

(71) Applicants: COMMISSARIAT A L'ENERGIE ATOMIQUE ET AUX ENERGIES ALTERNATIVES, Paris (FR); BIOMERIEUX, Marcy-l'Etoile (FR)

(72) Inventors: Francois Perraut, Saint Joseph de Riviere (FR); Pierre Joly, Grenoble (FR); Quentin Josso, Lyons (FR); Meike Kloster-Landsberg, Graefelfing (DE)

(73) Assignees: COMMISSARIAT A L'ENERGIE ATOMIQUE ET AUX ENERGIES ALTERNATIVES, Paris (FR); BIOMERIEUX, Marcy-l'Etoile (FR)

( * ) Notice: Subject to any disclaimer, the term of this patent is extended or adjusted under 35 U.S.C. 154(b) by 143 days.

(21) Appl. No.: 15/540,068

(22) PCT Filed: Oct. 23, 2015

(86) PCT No.: PCT/FR2015/052857
§ 371 (c)(1),
(2) Date: Jun. 27, 2017

(87) PCT Pub. No.: WO2016/107995
PCT Pub. Date: Jul. 7, 2016

(65) Prior Publication Data
US 2017/0363533 A1 Dec. 21, 2017

(30) Foreign Application Priority Data
Dec. 30, 2014 (FR) ...................................... 14 63445

(51) Int. Cl.
*G06K 9/00* (2006.01)
*G01N 15/14* (2006.01)
(Continued)

(52) U.S. Cl.
CPC ..... *G01N 15/1434* (2013.01); *G01N 15/1463* (2013.01); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 2009/0066934 A1 | 3/2009 | Gao et al. | |
| 2009/0091811 A1 | 4/2009 | Asundi et al. | |

(Continued)

FOREIGN PATENT DOCUMENTS

| | | |
|---|---|---|
| DE | 10 2005 036 326 A1 | 2/2007 |
| JP | 2012-504780 A | 2/2012 |

(Continued)

OTHER PUBLICATIONS

Nicolas Pavillon et al. ("Cell Optical Density and Molecular Composition Revealed by Simultaneous Mulitmodal Label-Free Imaging") (Year: 2013).*

(Continued)

*Primary Examiner* — Stephen P Coleman
(74) *Attorney, Agent, or Firm* — Oblon, McClelland, Maier & Neustadt, L.L.P.

(57) ABSTRACT

A system for analyzing a transparent particle including: an analysis pathway, including a first light source emitting an analysis light beam, and a first optical system focusing the analysis light beam in a focusing plane; and a position control pathway including a second light source, an image sensor, and a second optical system at least partially merged (Continued)

with the first optical system. The image sensor is offset relative to the image of the focusing plane by the second optical system. The system makes it possible to control correct positioning of the particle, even though it is transparent, and without disturbing the analysis pathway.

11 Claims, 9 Drawing Sheets

(51) Int. Cl.
    *G06T 7/00*     (2017.01)
    *G01N 15/10*     (2006.01)
    *G01N 15/00*     (2006.01)

(52) U.S. Cl.
    CPC ............ *G01N 2015/0065* (2013.01); *G01N 2015/1006* (2013.01); *G01N 2015/1452* (2013.01); *G06T 2207/10056* (2013.01); *G06T 2207/30024* (2013.01)

(56) References Cited

U.S. PATENT DOCUMENTS

| | | |
|---|---|---|
| 2009/0103082 A1 | 4/2009 | Black et al. |
| 2010/0261280 A1 | 10/2010 | Black et al. |
| 2013/0260396 A1 | 10/2013 | Akcakir |
| 2013/0274119 A1 | 10/2013 | Knutson et al. |
| 2015/0160613 A1* | 6/2015 | Ferraro ............... G03H 1/0443 359/32 |

FOREIGN PATENT DOCUMENTS

| | | |
|---|---|---|
| JP | 2013-83656 A | 5/2013 |
| JP | 2013-533469 A | 8/2013 |
| WO | WO 2011/149526 A2 | 12/2011 |

OTHER PUBLICATIONS

International Search Report dated Mar. 18, 2016 in PCT/FR2015/052857 filed Oct. 23, 2015.

French Search Report dated Oct. 21, 2015 in French Application 1463445 filed Dec. 30, 2014.

Nicolas Pavillon et al., "Cell Optical Density and Molecular Composition Revealed by Simultaneous Multimodal Label-Free Imaging", Biophysical Journal, Sep. 2013, vol. 105, No. 5, pp. 1123-1132, XP028712247.

Xiao Yu et al., "Review of digital holographic microscopy for three-dimensional profiling and tracking", Optical Engineering, 2014, vol. 53, No. 11, total pp. 22, XP060048121.

Patrik Langehanenberg et al., "Automated three-dimensional tracking of living cells by digital holographic microscopy", Journal of Biomedical Optics, 2009, vol. 14, No. 1, pp. 014018-1-014018-7, XP055043026.

Sang-Hyuk Lee et al., "Holographic microscopy of holographically trapped three-dimensional structures", Optics Express, 2007, vol. 15, No. 4, pp. 1505-1512.

Björn Kemper et al., "Methods and applications for marker-free quantitative digital holographic phase contrast imaging in life cell analysis", Proceedings of SPIE, 2007, vol. 6796, pp. 67960E-1-67960E-8, XP040249569.

Notice of Reasons for Refusal dated Apr. 22, 2019, in Japanese Patent Application No. 2017-534989, filed Oct. 23, 2015 (with English language translation).

\* cited by examiner

SYSTEM FOR ANALYSING A TRANSPARENT SAMPLE WITH CONTROL OF POSITION, AND ASSOCIATED METHOD

TECHNICAL FIELD

This invention relates, in a general manner, to the field of the optical analysis of transparent samples comprising specific points of interest. Said points of interest can in particular be biological particles, whereby the sample is therefore a biological sample.

The invention can in particular be applied for microbiological diagnosis, and more particularly for analysing micro-organisms by spectroscopy (in particular by Raman spectroscopy or by fluorescence spectroscopy) or even by diffraction or diffusion.

The invention concerns more particularly, however in a non-limiting manner, the analysis of particles transparent at the wavelength of an analysis light beam.

PRIOR ART

The analysis of small particles such as biological particles, and more particularly micro-organisms, can conventionally take place using an optical probe, known as an analysis pathway. This optical probe focuses an analysis light beam on the particle to be analysed, and measures a physical property of the beam after interaction with the particle, for example its Raman or fluorescence spectrum. The analysis of a particle can be used for the identification or characterisation thereof. The analysis light beam can be a laser beam, the waist of which is positioned on the particle, or a beam focused on the particle. The term "focusing spot" is used hereafter to describe the waist of a laser beam or the focusing spot of a beam, and both cases will refer to the focusing of an analysis beam.

The positioning of the focusing spot of the analysis beam on the particle to be analysed must be particularly precise, the size of said focusing spot being generally about the same as that of the particle to be analysed.

The positioning of the analysis beam on the particle, and more specifically of its focusing spot, is generally performed visually under a microscope. For this purpose, the system includes a position control pathway in addition to the analysis pathway described hereinabove. The position control pathway is used to control the position of a point of interest, in particular a particle, relative to the analysis pathway. In a phase preceding the measurement, the analysis pathway is configured such that, when a particle is located at the focusing point of the analysis pathway, the image thereof is sharp and at a position identified on the sensor of the control pathway.

Figure 1:
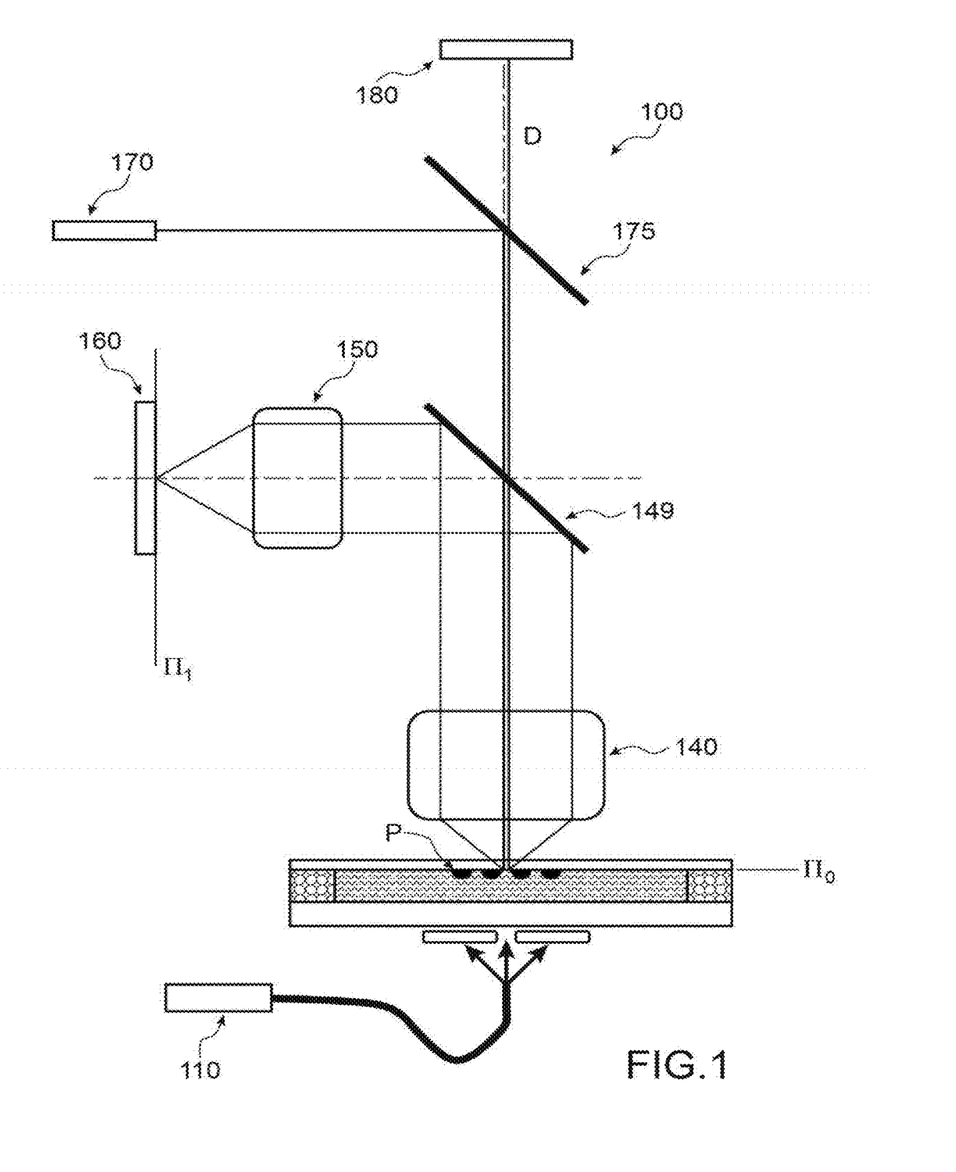
FIG. 1 shows, in a diagrammatic manner, an analysis system according to the prior art.

FIG. 1 shows one example of such an analysis system 100. In this example, the point of interest is a particle.

The analysis pathway comprises a first light source, for example a laser 170, used to illuminate a particle of interest. The beam emitted by the laser 170 is called an analysis light beam. The analysis pathway further comprises a first optical system 140, in this case constituted from a microscope objective. The optical axis of the first optical system 140 is referenced D.

In the example shown, the analysis pathway further comprises the measuring means 180 for measuring a physical property of said beam after it has interacted with a particle P.

The microscope objective focuses the waist of the laser beam in the focusing plane $\Pi_0$. A beam-splitting plate 175 (for example a dichroic plate) splits the beam emitted by the laser source and the beam having interacted with the particle P.

The position control pathway comprises a light source 110 for illuminating the particle P, the microscope objective 140, a tube lens 150 and an image sensor 160. At the output of the objective 140, the image of the particle formed by the light source 110 is extended to infinity, then projected onto the plane of the sensor 160 by the tube lens 150.

The analysis pathway and the position control pathway share the same microscope objective and the same focusing plane $\Pi_0$, thanks to a deflecting mirror 149. Either of the pathways is used alternatively.

The correspondence between the two pathways is made during an adjustment phase prior to the measurement. For example, it consists in placing a control object for controlling the analysis beam (for example an opaque structured focusing pattern) at the maximal focusing point, by maximising the signal obtained on the measuring means 180. The position of the sensor 160 of the control pathway is then adjusted so as to produce a sharp image of the control object, at an identified position of said sensor of the control pathway.

At the time of taking a measurement on a particle of a sample, the positioning of said particle at the focal point of the analysis beam takes place according to the following two steps.

In a first step, the laser 170 is switched off, the light source 110 is switched on, the deflecting mirror 149 is positioned, and an image is acquired of the focusing plane using the image sensor. When the particle is sharp in said image, this particle is located in the focusing plane. The positioning of the particle is then laterally finalised on the identification point determined during the instrument adjustment phase described hereinabove.

In a second step, the light source 110 is switched off, the laser 170 is switched on and the deflecting mirror 149 is removed. If the particle has not moved, the focusing spot of the analysis beam is located on said particle.

However, the positioning is made difficult, or even impossible, when the particle is transparent in the visible spectrum. In the description hereafter, the term transparent particle shall describe a particle that has a very low degree of visible light absorption (i.e. a transmission coefficient of greater than or equal to 70% in the visible spectrum or more generally in a spectral band from 300 nm to 1000 nm) and a low difference in refractive index with its surrounding environment (for example an index difference of less than 0.1). Certain cells (unlabelled eukaryotic and prokaryotic cells), and certain particles made from dielectric materials can therefore be qualified as transparent.

One known solution consists in temporarily displacing the particle P. The substrate receiving the biological particle is therefore mounted on a translation stage for translation along an axis that is parallel to the optical axis of the objective 140.

This consists in dividing the second step described hereinabove into two sub-steps.

In the first sub-step, the position control pathway is used in defocusing conditions. In other words, the particle is offset along the optical axis of the microscope objective so that it is no longer in the focusing plane thereof.

This defocusing allows a non-sharp image of the particle P to be obtained, in which the transparent particle can nonetheless be distinguished from the surrounding environment. The lateral position of the particle P can therefore be known in a plane perpendicular to the optical axis of the objective.

In the second sub-step, the particle is repositioned in the focusing plane of the microscope objective. The image of the particle is lost on the position control pathway, however the analysis beam focusing spot is on the particle.

One drawback of this solution is that if the particle has moved, migrated or separated from its substrate (for example in cases of bacteria captured by a substrate) between the first sub-step and the measurement, the particle is no longer at the focusing point of the analysis beam at the time of the measurement. The integrity of the analysis cannot therefore be guaranteed, and it is even less possible to dynamically control with feedback the analysis beam on the position of the particle.

The purpose of this invention is therefore to allow for the position of a particle to be controlled in real time, specifically that of a transparent particle, in particular in order to guarantee the reliability of the analysis thereof using an analysis light beam.

DESCRIPTION OF THE INVENTION

This invention relates to a system for analysing a particle of interest of a sample comprising:

an analysis pathway, comprising a first light source emitting an analysis light beam, and a first optical system arranged so as to focus the analysis light beam in a plane orthogonal to the optical axis thereof, called a focusing plane; and a position control pathway, comprising a second light source, an image sensor, and a second optical system at least partially merged with the first optical system such that the first optical system and the second optical system comprise the same so-called shared optical system.

According to the invention, the image sensor is offset relative to the image of the focusing plane by the second optical system.

The defocused image obtained by the image sensor is used to obtain to check that the particle is correctly located in an expected position. This check can perform a simple comparison with a defocused image obtained when the particle is located in said target position.

The invention does not require any intermediate step involving moving the microscope objective or the sample.

The defocused image and the pointing of the focusing spot can be obtained simultaneously, or successively however within a very short time interval. This guarantees the reliability of the analysis, as a displacement of the particle is detected before each operation for pointing the focusing spot at the position in which said particle must be located.

Moreover, the pointing of an analysis laser beam at a particle provides energy that can separate the particle from a substrate to which it is bonded. The system according to the invention allows it to be easily checked that the positioning of the focusing spot on the particle has not caused the particle to move.

Preferably, the analysis system according to the invention includes computing means configured to compute, by numerical propagation, at least one image, reconstructed from an image provided by the image sensor.

The defocused image obtained by the image sensor thus allows an image to be obtained, by computation, said image being associated with a virtual position of the image sensor that is different to its real position. The term virtual position is used because, in reality, the image sensor remains immobile and the displacement thereof is only simulated digitally. As described hereinbelow, the particle of interest can therefore be positioned in a precise manner.

The analysis system can comprise partial and/or selective deflection means, arranged so as to combine the position control pathway and the analysis pathway at the input to the shared optical system.

Alternatively, the first light source and the second light source have different wavelengths, and the deflection means are wavelength-selective means.

According to one advantageous embodiment, the computing means receive at the input thereto an image provided by the image sensor, and are configured to compute, based on the image provided by the image sensor and by numerical propagation, a reconstructed image of the particle of interest in the image $\Pi_1$ of the focusing plane $\Pi_0$.

The computing means can receive at the input thereto an image provided by the image sensor, and can be configured to compute, based on the image provided by the image sensor and by numerical propagation, a series of reconstructed images in reconstruction planes, each of which is offset relative to the plane of the image sensor.

The computing means advantageously comprise means for determining, based on said series of reconstructed images, an offset relative to the plane of the image sensor, called an optimum offset, associated with a minimum offset between the reconstruction plane and a plane receiving the image of the particle of interest by way of the second optical system.

The computing means preferably comprise means for comparing the optimum offset with the distance between the plane of the image sensor and the image of the focusing plane by the second optical system, the result of the comparison determining an axial displacement command, and the analysis system comprises displacement means configured to move a support for receiving the sample, in response to said axial displacement command.

The computing means can comprise means for comparing a control image with a reconstructed image called focused image, the focused image being associated with a minimum offset between a position of a corresponding reconstruction plane, and a plane receiving the image of the particle of interest by way of the second optical system.

The analysis system advantageously comprises means for thresholding a reconstructed image, the threshold being defined by $i_{th}=i_{av}+3\sigma$ where $i_{av}$ is the mean value of the intensity of the pixels in the reconstructed image and $\sigma$ is the standard deviation of the intensity of the pixels in the reconstructed image.

According to one advantageous embodiment, the result of the comparison of the control image and the focused image determines a transverse displacement command, and the analysis system comprises displacement means configured to move a support for receiving the sample, in response to said transverse displacement command.

The invention further relates to a method for analysing a particle of interest of a biological sample, implemented within a system according to the invention, comprising a step of analysing the particle of interest using the analysis pathway, and a step of controlling the position of the particle of interest using the position control pathway. According to the invention, the implementation of these two steps is not separated by an intermediary step for moving the sample relative to the analysis and position control pathways.

Preferably, the analysis and position control steps are implemented simultaneously.

According to one preferred embodiment, the position control step comprises the sub-steps of:

acquiring an image of the particle of interest using the image sensor of the position control pathway;

using said image, constructing, by numerical propagation, at least one reconstructed image, in a reconstruction plane that is offset relative to the plane of the image sensor.

The method according to the invention can include a computation of a series of reconstructed images in reconstruction planes, each of which is offset relative to the plane of the image sensor, and a selection of the reconstructed image associated with the minimum offset between the corresponding reconstruction plane and a plane receiving the image of the particles by way of the second optical system.

The method according to the invention preferably comprises a computation of a reconstructed image of the particle of interest in the image of the focusing plane.

BRIEF DESCRIPTION OF THE FIGURES

Other characteristics and advantages of the invention shall appear upon reading the following preferred embodiments given with reference to the accompanying figures, in which.

DETAILED DESCRIPTION OF THE SPECIFIC EMBODIMENTS

An analysis system is initially described according to the invention, in addition to an analysis method implemented in such a system.

Figure 2:
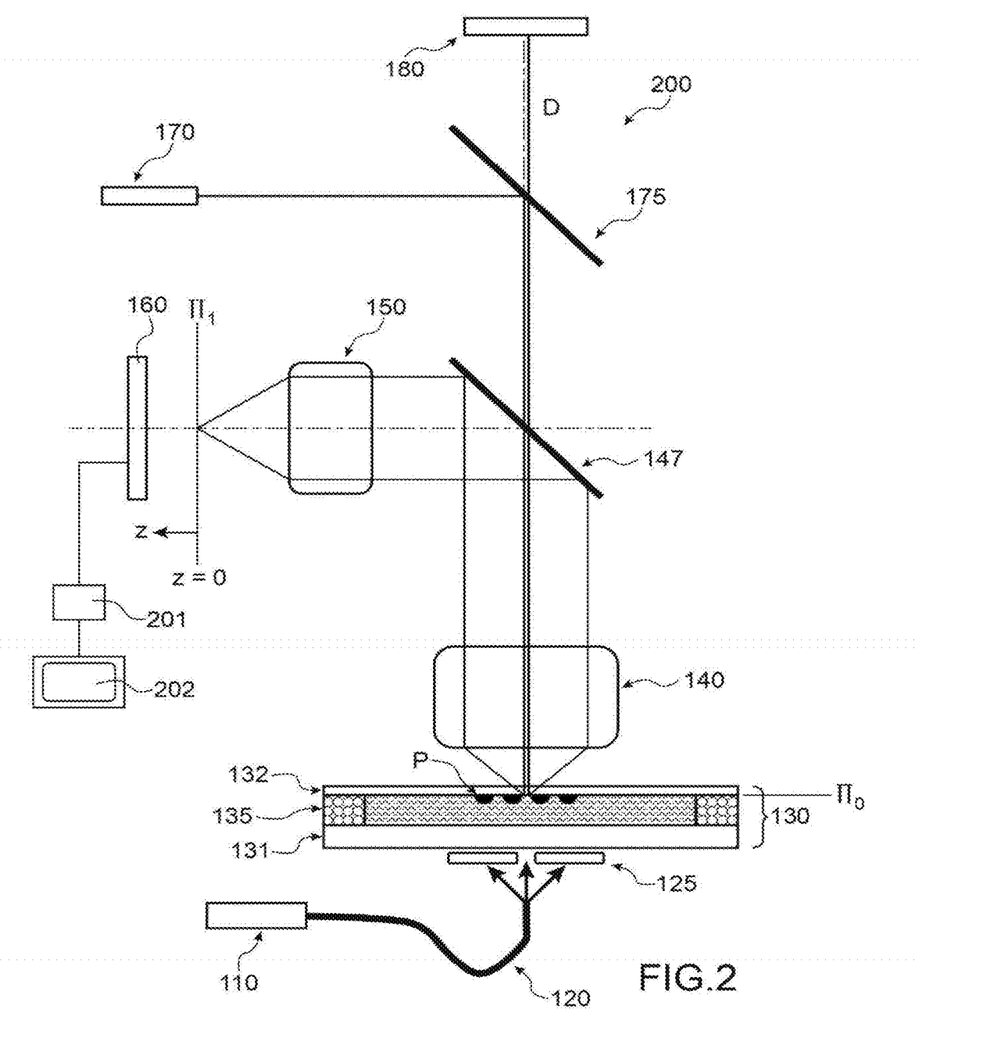
FIG. 2 shows, in a diagrammatic manner, a first embodiment of an analysis system according to the invention.

FIG. 2 shows a first embodiment of an analysis system according to the invention, for the visual control of the position of a particle, in particular a transparent particle.

This analysis system 200 comprises a first so-called analysis pathway and a second so-called position control pathway. The system 200 will only be described for its differences with the system in FIG. 1.

The sample can be present in the form of a liquid medium such as water, a buffer solution, a culture medium or a reactive medium containing particles. The particles are advantageously fixed to a substrate such as a microscope slide.

Alternatively, the sample can be present in the form of a solid medium such as agar containing the particles in question. The particles can be located inside the medium or on the surface of the sample.

Alternatively, the sample can be present in the form of a gaseous medium, whereby the particles are located in this medium or preferably fixed to a substrate such as a microscope slide.

The particles to be analysed P can be biological particles, dust (for example pollutants) or even dielectric material particles. The invention is particularly advantageous when said particles are transparent as defined hereinabove.

In the case of a liquid sample, the sample can be encased in an analysis chamber 130 vertically delimited by a lower plate 131, for example a conventional microscope slide, and an upper plate 132 (for example a microscope cover slip). The analysis chamber is laterally delimited by a tight seal 135. The lower and upper plates are transparent to the wavelengths of the first and second light sources (see below).

Advantageously, the analysis system according to the invention comprises a motorised support (not shown) for receiving the sample containing the particle of interest.

The analysis beam emitted by the laser 170 is reflected towards the sample by the first beam-splitting plate 175. After reflection on the plate 175, the analysis beam is aligned along the optical axis D. The analysis beam passes through a second dichroic plate 147, the advantage of which is described hereafter, then the first optical system 140, and finally reaches the sample, and in particular the particle of interest P*. Upstream of the first optical system 140, the analysis beam is a collimated laser beam.

The focusing plane $\Pi_O$ is the plane orthogonal to the optical axis D, in which is located the waist of the analysis laser beam formed by the first optical system 140. This plane $\Pi_O$ corresponds in this case to the object focal plane of the first optical system 140. In the embodiment shown in FIG. 2, it is assumed that the particles, and in particular the particle of interest, are found in the focusing plane $\Pi_O$.

At least one part of the analysis beam that has interacted with the particle of interest P* returns to the first optical system 140. This backscattered analysis beam passes back through the first optical system 140, the second beam-splitting plate 147, then the first beam-splitting plate 175, in order to be analysed by the measuring means 180.

These measuring means 180 carry out the measurement of a property of the analysis beam having interacted with the particle of interest. These measuring means 180 can in particular include a spectrometer or an image detector, in order to perform Raman spectrometry or a fluorescence measurement. The measuring means can include focusing means, not shown, in order to focus the analysis beam having interacted with the particle of interest on a sensor.

The position control pathway includes the second light source 110, that is preferably spatially coherent, and possibly temporally coherent. Preferably, the first source has a low spectral bandwidth, for example less than 200 nm, or even less than 100 nm or 25 nm. This light source can in particular be a laser diode or a light-emitting diode. For convenience, the light beam emitted by the source can be provided by means of an optical fibre 120 beneath the sample to be analysed (on the opposite side to the first optical system 140). Where necessary, the beam emitted by the fibre is limited by means of a diaphragm 125. The beam emitted by the second light source is called a control light beam.

The position control pathway further comprises a second optical system comprising the microscope objective 140 and the lens 150, called a tube lens.

The second optical system shares the microscope objective 140 with the first optical system. The first optical system and the second optical system are partially merged. The microscope objective 140 forms a so-called shared optical system, belonging both to the analysis pathway and the position control pathway. This sharing is permanent, whereby the removable deflecting mirror 149 is replaced by partial and/or selective deflecting means, in this case the second dichroic plate 147 that implements a wavelength-selective deflection.

The second optical system optionally comprises an optical filter (not shown) that can be situated in front of or behind the objective.

After diffraction by the particle of interest P*, the control light beam passes through the shared optical system (microscope objective 140), then is reflected by the dichroic plate 147. This beam then passes through the tube lens 150, before reaching an image sensor 160, for example the CCD or CMOS sensor of a camera.

The particle of interest P* is located in the focusing plane $\Pi_O$, in this case the object focal plane of the microscope objective 140. The beam diffracted by the particle of interest P* is therefore extended to infinity by the microscope objective. The tube lens 150 is used to focus this beam in a plane $\Pi_I$. The plane $\Pi_I$ is the image of the focusing plane $\Pi_O$ by the second optical system (objective 140 and lens 150). These two planes are conjugated by the objective and the lens 150.

According to the invention, the image sensor 160 is not located in this image plane $\Pi_I$, but is offset relative to this plane. It is offset along the optical axis of the second optical system. This offset is, for example, between +1 µm and +200 mm, or −1 µm and −200 mm, for example between +10 µm and +5 mm, or −10 µm and −5 mm, or between +5 µm and +1000 µm, or −5 µm and −1000 µm, preferably between +10 µm and +2000 µm, or −10 µm and −2000 µm.

The optical axis of the tube lens 150 and the optical axis of the objective 140 are merged, whereby the plate 147 simply makes it possible that this axis does not extend in a straight line. The sensor is located in a plane orthogonal to said optical axis. Where Z is a coordinate along said optical axis, the origin of which is located in the plane $\Pi_I$, Z=z represents the defocusing distance of the image sensor 160. The X and Y axes define with Z an orthogonal coordinate system.

The image sensor 160 acquires a transmission image of the particle of interest. The image formed on the image sensor is a holographic image insofar as it is the result of the interference between a wave diffracted by the particles and a reference wave that has passed through the sample without having interacted with it.

The image acquired by the image sensor 160 allows, in an indirect manner, to control the position of a particle of interest, even if it is a transparent particle. Different control examples are disclosed hereafter.

In the embodiment shown in FIG. 2, the control pathway and the analysis pathway undergo wavelength division multiplexing by the dichroic plate 147. The first and second light sources have disjoint spectra. For example, the second light source is a GaInN laser diode with a spectrum centred at about 450 nm and the first light source is a frequency-doubled YAG laser emitting at 532 nm. The dichroic plate 147 reflects the light at 450 nm towards the image sensor 160, and allows it to pass at 532 nm. (If the measuring means 180 are formed from a Raman spectrometer, the beam-splitting plate 175 is chosen to reflect the light at 532 nm and allow greater wavelengths to pass).

Wavelength division multiplexing has the advantage of allowing to determine the position of the particle of interest in real time and at the same time as the analysis. This allows the position of the analysis laser beam on the particle of interest to be controlled with feedback with a very low time constant.

Alternatively, the position control pathway and the analysis pathway are temporally multiplexed. During a first time interval, the position of the particle of interest is controlled by means of the light source 110, the light source 170 thus being switched off. In a second time interval, the light source 110 is switched off and the light source 170 is switched on, and the particle is analysed.

The plate 147 can be a semi-reflective plate, more particularly but not exclusively adapted to temporal multiplexing.

In all cases, the particle of interest is not displaced relative to the first and second optical systems, between the position control and analysis. These two steps can therefore be performed simultaneously, or at least within a very short time interval. This objective is reached when the position control and analysis pathways are fixed relative to each other.

According to an alternative embodiment, not shown, the image sensor is fixed on a translating device for translation along the optical axis of the second optical system, in order to position it at an optimum defocusing distance that depends on the optical properties of the objective 140 and of the tube lens 150.

According to another alternative embodiment, not shown, the first light source 170 emits a non-collimated beam. The first optical system comprises a lens that engages with the objective 140 in order to position the focusing spot in a focusing plane $\Pi_O$ that is not necessarily the object focal plane of the objective 140. In such a case, the properties of the tube lens 150 can be adapted.

The control and analysis pathways can be inverted, whereby the beam-splitting plate 147 deflects the position control light beam, and reflects the analysis light beam having interacted with the particle of interest.

The tube lens 150 can be positioned between the sensor 160 of the position control pathway and the beam-splitting plate 147, as shown in FIG. 2, or between the beam-splitting plate 147 and the microscope objective 140. In such a case, the tube lens 150 and the objective 140 are shared by the first and the second optical system, which requires adapting the rest of the first optical system.

It is assumed in this case that a priori information is available on the relative position of the particles of the sample. After locating the particles, a particle of interest P* is selected therefrom for analysis. It is assumed hereafter that the particle of interest has been placed in a target position usually taken on the optical axis and in the focusing plane. The position of the particle of interest can shift over time. The invention is designed to determine whether the position of the particle has changed and, where necessary, to bring the particle of interest back to said target position. A displacement of the particle along the XY plane will firstly be examined.

The computing means 201 (for example a processor) receive the image formed on the image sensor 160.

The computing means 201 use this image to compute, by numerical propagation, a reconstructed image of the sample, and more particularly of the particle of interest, in a reconstruction plane that is offset from the plane of the detection surface of the image sensor. The description below will more simply state a reconstruction plane associated with an offset relative to the plane of the image sensor. In other words, an offset of the sensor relative to the effective position thereof is simulated by the computation of said reconstructed image.

The image acquired by the sensor can be standardised before application of the propagation operator. The DC component thereof can also be extracted therefrom.

A description of an image computation method by numerical propagation can be found in the article by Sang-Hyuk Lee et al. entitled "*Holographic microscopy of holographically trapped three-dimensional structures*" published in the Optics Express, Vol. 15; No. 4, 19 Feb. 2007, pp. 1505-1512.

For example, if the Rayleigh-Sommerfeld propagation function is written as $h_z(r)$, i.e.:

$$h_z(r) = -\frac{1}{2\pi}\frac{\partial}{\partial z}\frac{e^{ikR}}{R} \quad (1)$$

where:

z is the distance between a "virtual" position of the image sensor and the effective position thereof, or in other words the offset between the reconstruction plane and the plane of the image sensor, r=(x,y) is the position in the plane of the image provided by the sensor, $R^2 = r^2 + z^2$ and k=2πn/λ is the wave number relative to the propagation medium.

The distance z is chosen herein such that the reconstruction plane is located in the plane $\Pi_f$, or substantially in said plane (for example as a function of a minimum translation step of the sensor). In any case, the reconstruction plane associated with the reconstructed image is closer to the plane $U_I$ than the plane of the image sensor.

The wave in the coordinate plane z can be expressed as follows:

$$a(r, z) = |a(r, z)|\exp(i\varphi(r, z)) \quad (2\text{-}1)$$

$$a(r, z) = \frac{1}{4\pi^2}\int_{-\infty}^{+\infty} B(q)H_{-z}(q)\exp(iqr)d^2q \quad (2\text{-}2)$$

where:

B(q) is the Fourier transform of b(r), the intensity of the diffracted wave at the effective position of the sensor (the intensity of the reference wave is assumed herein to be constant), $H_{-z}(q)$ is the Fourier transform of $h_{-z}(r)$ and q is the dual variable of r in the Fourier transform.

An intermediate reconstructed image is computed, the value of each pixel of which is defined by the complex amplitude $a(r,z_n)$. This image is a complex image, whereby each pixel is associated with a complex value with a real part and an imaginary part.

The reconstructed image is built from this intermediate reconstructed image for presentation to the user. The reconstructed image is defined based on the complex amplitude $a(r,z_n)$. Each pixel of the reconstructed image can be defined by $|a(r,z_n)|^2$, the squared modulus of the complex amplitude. Alternatively, each pixel can be defined by $|\Im(a(r,z_n))|^2$, the square of the imaginary part of the complex amplitude.

The particles can be easily identified in the reconstructed image, even though they are transparent. This would not be the case on a real image, obtained not by simulating a positioning of the image sensor in the plane $\Pi_f$, but by effectively positioning the sensor in said plane.

The reconstructed image is fed to a display screen 202.

Figure 4A:
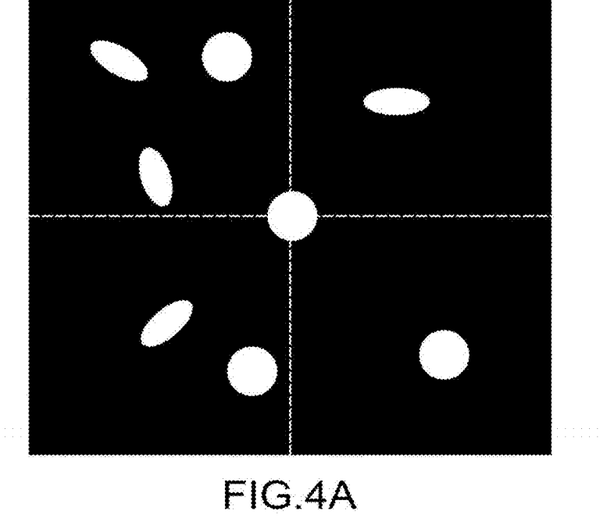
FIGS. 4A and 4B show, in a diagrammatic manner, a thresholded reconstructed image and a thresholded, processed reconstructed image, in order to locate a particle.

The processor 201 can perform a thresholding of the reconstructed image, whereby the threshold is, for example, defined by:

$$i_{th} = i_{av} + 3\sigma \quad (3)$$

where $i_{av}$ and σ are the mean value and standard deviation respectively of the intensity in the reconstructed image. The image is obtained as shown in FIG. 4A. The presence of a particle at a target position can be checked by comparing the intensity of the reconstructed image at this point with said threshold value.

Figure 4B:
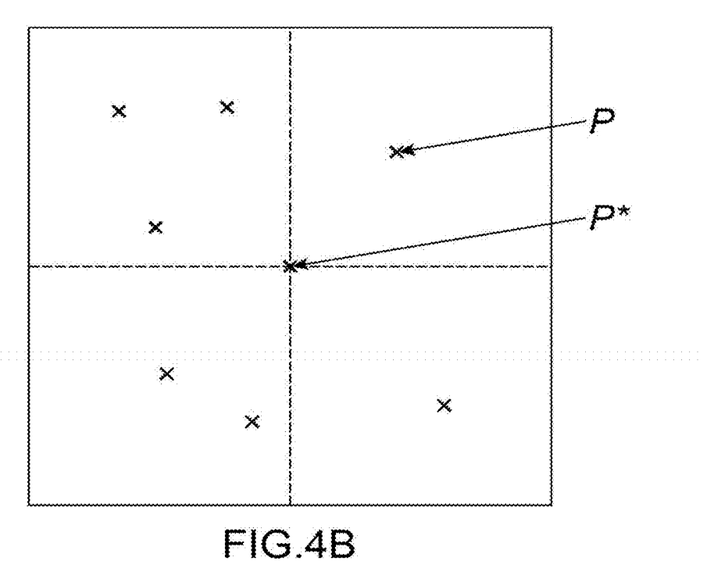

Thresholding can be complemented by a contour detection process and morphological filtering operations (opening, closing). Thanks to these operations, the objects not corresponding to particles are excluded from the image. Moreover, the reconstructed image can thus be presented in the form of a distribution of points, each of which corresponds to the centre of a particle. This distribution of points is shown in FIG. 4B.

The display of a reconstructed image thus processed allows the user to easily check that a particle is present in the expected location. The absence of any particle near the target position can originate from the fact that it has become separated from its substrate. The display screen can display a symbol such as a focusing pattern in order to quickly compare the position of the particle of interest along the X and Y axes with a target.

The position control of the particle of interest can consist, as is the case herein, in the display of the reconstructed image associated with the image plane $\Pi_f$. Additionally or alternatively, this control includes the supply of information on the presence or absence of the particle of interest in the expected position, and/or the supply of information on a displacement of the particle of interest relative to its expected position.

Figure 3:
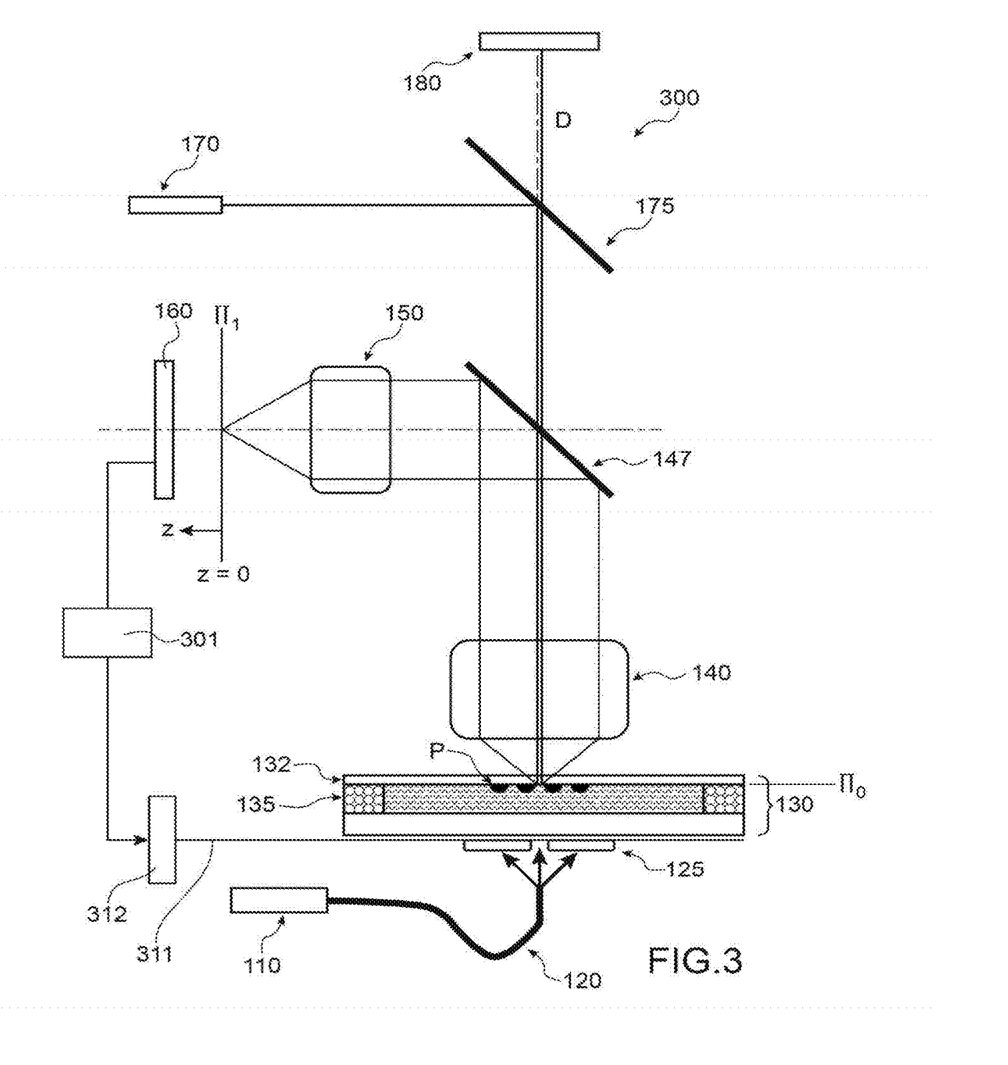
FIG. 3 shows, in a diagrammatic manner, a second embodiment of an analysis system according to the invention.

FIG. 3 shows, in a diagrammatic manner, a second embodiment of the analysis system 300 according to the invention. FIG. 3 will only be described for its differences relative to FIG. 2.

The computing means 201 and the screen 202 are replaced by computing means 301 such as a processor, and displacement means 312 for moving a support 311 receiving the sample.

The displacement means 312 consist, for example, in a translation stage for translation along the X and Y axes, and where relevant a translation stage for translation along the Z axis.

The image detected by the sensor 160 is provided to the processor 301 forming means for computing a displacement command. The displacement command is fed to the displacement means 312. The displacement command is determined according to a measured displacement of the particle of interest relative to a target position, and is intended to reposition said particle in the target position.

The processor 301 carries out a computation of a series of reconstructed images, each of which is associated with a predetermined offset between a "virtual" position of the image sensor and the effective position thereof, or in other words between a reconstruction plane and the plane of the image sensor. The reconstruction planes are distributed on either side of the expected position of the image, by the second optical system, of the plane receiving the particle of interest (in this case on either side of the image plane $\Pi_I$). For example, the series of reconstruction planes scans an interval of +/−50 µm around the plane $\Pi_I$, with a step of 2.5 µm corresponding, if using a transverse magnification of 100, to a displacement of the image of the sensor in the space of the object of +/−5 µm around the plane $\Pi_O$, with a step of 0.25 µm.

Each reconstructed image is computed based on the same image acquired by the image sensor according to the algorithm explained hereinabove. Said reconstructed images are those that would be observed for different positions $z_1, \ldots, z_N$ of the image sensor. A series of reconstructed images $I_1, \ldots, I_N$ is obtained.

Figure 5:
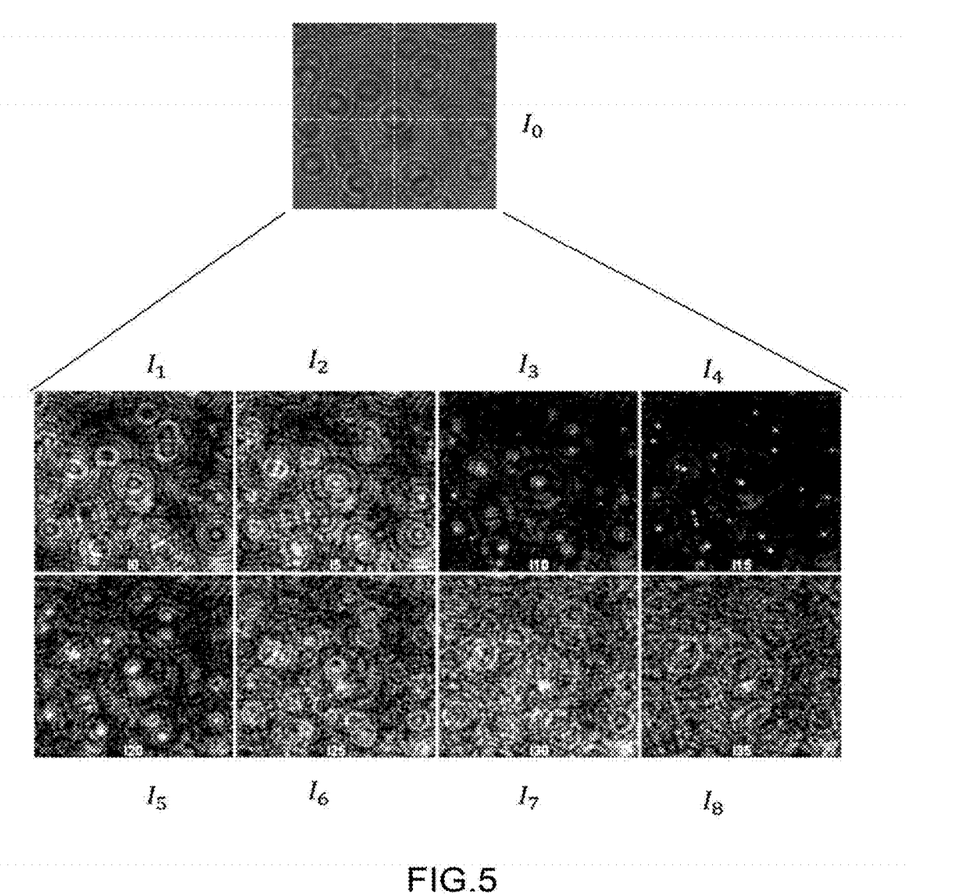
FIG. 5 shows the obtaining of a series of reconstructed images according to the invention.

FIG. 5 shows a series of reconstructed images $I_1, \ldots, I_N$ obtained based on an image $I_0$ acquired by the image sensor.

The processor uses said reconstructed images to determine the displacement of the particle of interest relative to its target position, along the Z axis, then along the X and Y axes. The target position corresponds, for example, to the focusing point of an analysis laser beam.

Steps are firstly described for determining said displacement of the particle of interest along the Z axis.

A singular point of a function is sought, describing the evolution of a parameter of the reconstructed images, depending on the position of the reconstruction plane along the Z axis. Alternatively, the function depends on the position of the reconstruction plane, brought into the object plane of the second optical system.

This parameter is advantageously representative of the contrast of the reconstructed images, for example the standard deviation or the mean value of the gradient in a predetermined area. The singular point is advantageously a maximum, however it can also be an inflection point. This singular point corresponds to a reconstruction plane located in the plane image of the plane receiving the particles, and more particularly the particle of interest. Therefore, a displacement of the particles along the Z axis is determined, by measuring the displacement of the image of the plane receiving said particles.

The displacement of the particle of interest along the Z axis, relative to the target position, is advantageously calculated directly in the object space, by introducing the physical parameters of the second optical system, for example its magnification.

Figure 6:
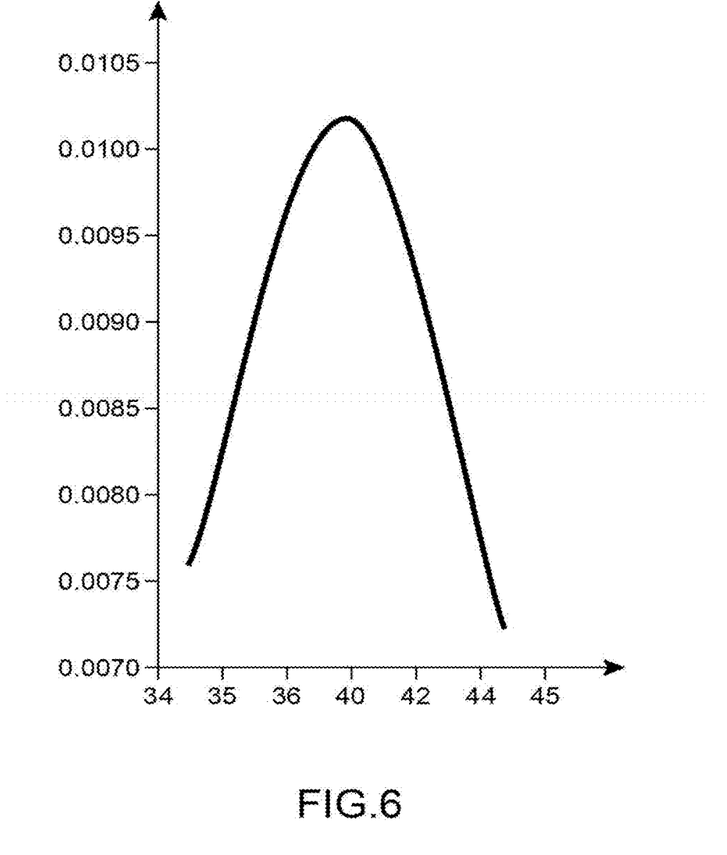
FIG. 6 shows, for a series of reconstructed images, a curve giving the standard deviation in the image as a function of an offset associated with said image.

FIG. 6 shows a curve giving the standard deviation in an image of the series as a function of the offset, brought into the object space, between the plane of the image sensor and the reconstruction plane.

The plane of the target position is in this case the plane $\Pi_I$, corresponding to the plane $\Pi_O$ in the object space of the second optical system. This plane is located approximately in z'=40 µm, where z' is an offset, brought into said object space, between the plane of the image sensor and the reconstruction plane.

The standard deviation values are obtained for discrete offset values $z'_n$, and said standard deviation values are interpolated, for example using a spline function, to obtain a standard deviation curve C(z') as a function of the offset z'. $z'_{foc}=\mathrm{argmax}(C(z))$ is determined, then is compared to a setpoint value of $z'_{foc}$ to calculate a displacement in the object space of the second optical system.

Alternatively, a displacement in the image space is firstly determined, then the corresponding displacement in the object space of the second optical system is calculated.

The value of $z'_{foc}$ does not necessarily correspond to an image effectively reconstructed. This can merely be a relatively rough sampling interval of the reconstruction planes, which requires less calculation due to the low number of images to be reconstructed.

Alternatively, no interpolation is performed, so that the determination of $z'_{foc}$ corresponds to the selection, in the series of reconstructed images, of the image that is the closest to the focusing conditions. This image is that which is the closest to the plane of the image of the particles by the second optical system. Said image is called a focused image $I_{foc}$.

Alternatively, a first approximate determination is performed of the position along the Z axis using a first sampling interval and a first series of reconstructed images, then said determination is refined using a narrower sampling interval and a second series of reconstructed images centred on the previously determined approximate position.

Preferably, the position of the particle of interest is determined along the Z axis using a series of reconstructed images of a region of interest centred on the particle of interest. Indeed, the particles are not necessarily all in the same plane orthogonal to the optical axis. For this purpose, a first series of images can be computed, the focused image $I_{foc}$ can be selected and used to determine an approximate position of the particle of interest along the X and Y axes, then a precise determination of the position of the particle of interest along the Z axis can take place using a series of reconstructed images centred on the particle of interest.

The size of the region of interest can be larger or smaller than that of the particle to be analysed.

Figure 7:
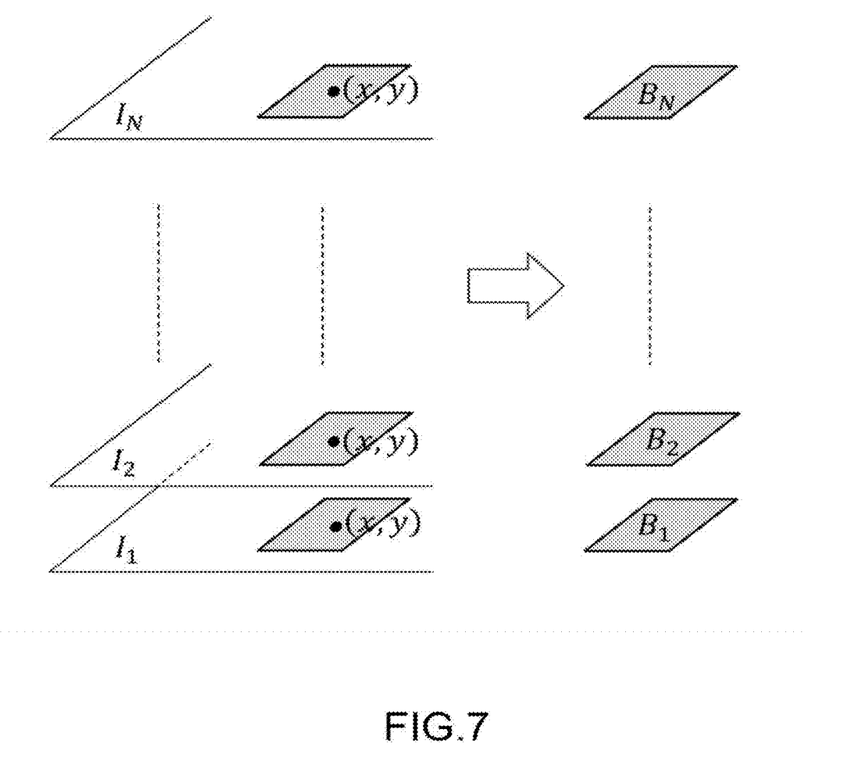
FIG. 7 shows, in a diagrammatic manner, the extraction of a series of reconstructed images of a region of interest, from a series of reconstructed images of a sample.

FIG. 7 shows, in a diagrammatic manner, a series of images $I_1, \ldots, I_N$ and a series $B_1, \ldots, B_N$ of reconstructed images of the region of interest, centred on a particle of interest P.

Figure 8:
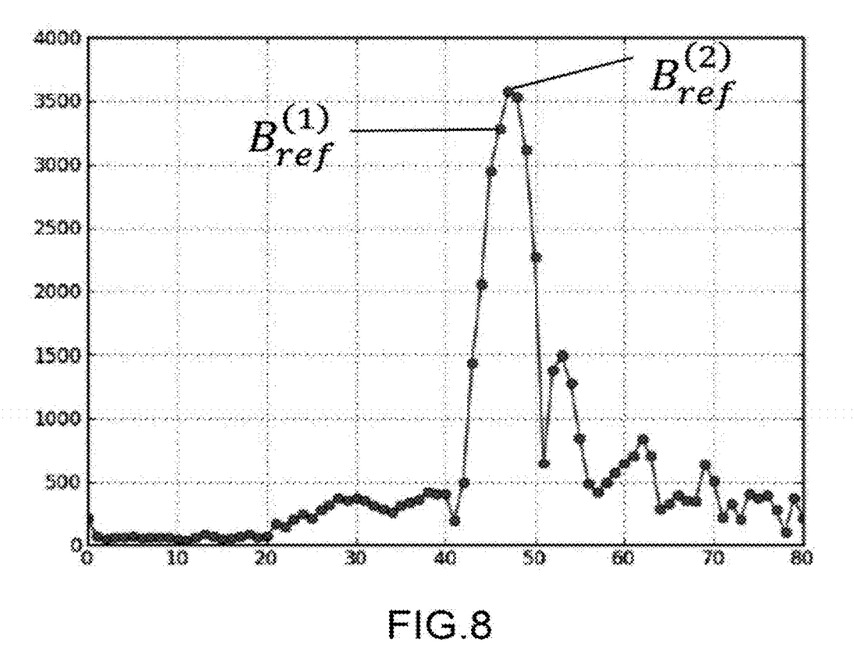
FIG. 8 shows, in a diagrammatic manner, a standard deviation curve in a series of reconstructed images of a region of interest, as a function of an offset associated with each image.

FIG. 8 shows the curve giving the standard deviation in a series of reconstructed images of the region of interest, as a function of the rank of the image of the series. $B_{ref}^{(1)}$ is associated with the region of interest on the focused image $I_{foc}$, the focused image associated with the whole sample. $B_{ref}^{(2)}$ corresponds to the reconstructed image of the region of interest having the maximum standard deviation. It is understood that the first selection $B_{ref}^{(1)}$ that was optimal on the focused image is no longer optimal when the contrast measurement is limited to the region of interest.

One of ordinary skill in the art will obtain more details on this localisation in the patent application FR1460947. Offsets in the object space and offsets in the image space are connected by a simple magnification ratio.

Once the displacement along the Z axis has been calculated, a displacement of the particle of interest along the XY plane is estimated.

To achieve this, a reconstructed image is used, associated with a reconstruction plane at a coordinate corresponding to the position of the plane $\Pi_I$ corrected of the previously determined displacement along the Z axis. This image can be selected from among the series of previously reconstructed images, or can be expressly reconstructed (for example if the displacement along the Z axis has been determined using an interpolation).

The processor 301 compares this reconstructed image (that has potentially undergone thresholding and filtering as described with reference to FIG. 2), with a control image wherein each particle is represented at its target position.

The control image forms a distribution plan of the particles in the sample. The control image can have been initially determined in the same manner as the reconstructed image with which it is then compared.

The estimation of the displacement can implement an image registration method, for example a cross-correlation between the control image and the reconstructed image, or a minimisation of the root mean square deviation between said images, or a minimisation of the mutual information between said images.

An axial displacement along the Z axis and a transverse displacement along the XY plane are therefore ultimately obtained. Using said displacement, the processor 301 formulates a displacement command that it feeds to the displacement means 312 in order to bring the particle of interest to the target position.

The focusing spot of the analysis laser beam on the particle of interest can thus be controlled with feedback.

The invention therefore bypasses an explicit determination of the position of the particles, as a simple image comparison is used to determine a transverse displacement of the particle.

Alternatively, the position of the particle of interest can be explicitly determined for comparison with a target position.

Preferably, the reconstructed image comprises multiple particles, including the particle of interest. The position of multiple particles around the particle of interest is checked in order to ensure the correct particle of interest is being observed.

Figure 9:
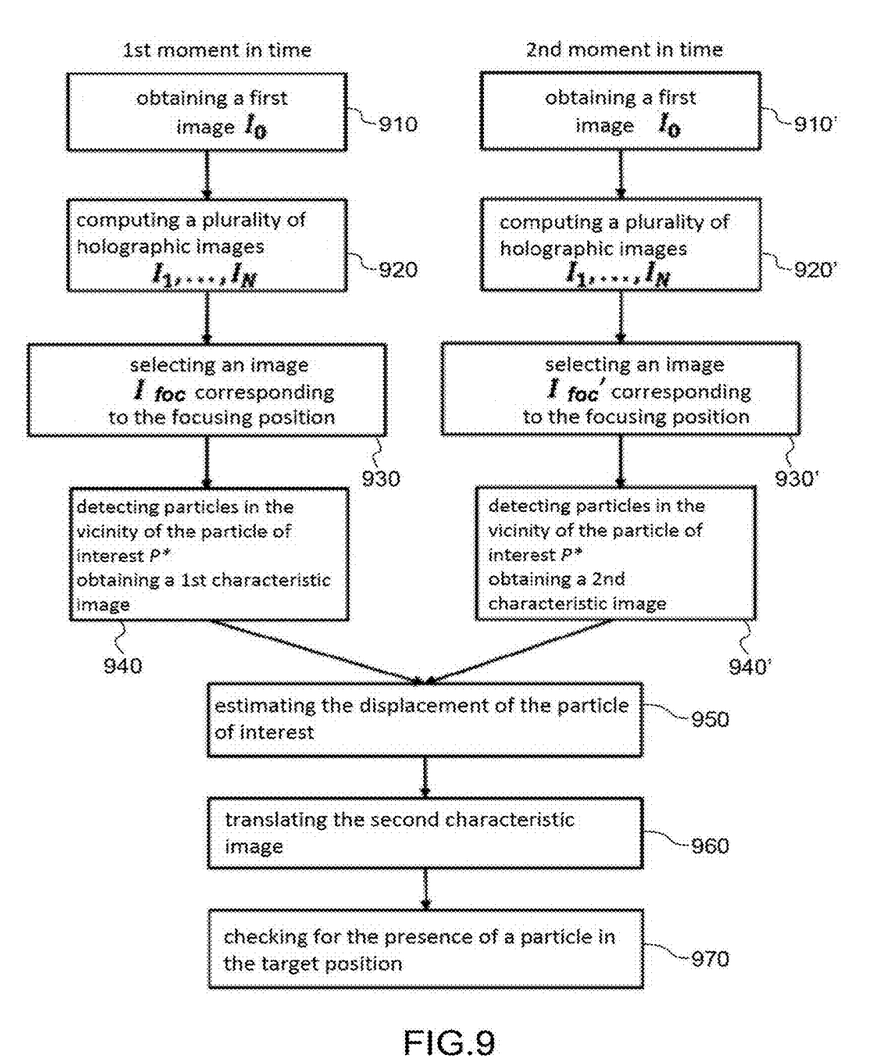
FIG. 9 shows, in a diagrammatic manner, steps implementated within a method according to the invention, to ensure the correct positioning of the focusing spot of the analysis light beam.

This description shall now disclose, with reference to FIG. 9, the steps of a method for determining a displacement of the particles between two moments in time, directly from the defocused images acquired by the image sensor. This method is implemented within an analysis system according to the invention, provided with a translation stage for translation along the X and Y axes.

In step 910, an initial image $I_0$ of the sample is acquired at a first moment in time by means of the control pathway. A plurality of reconstructed images $I_1, \ldots, I_N$ is then reconstructed based on the image $I_0$ (step 920), and a focused image $I_{foc}$ is selected, said focused image corresponding to the position of the image of the plane receiving the particle of interest, through the second optical system (step 930). A thresholding operation is then performed as described hereinabove on the focused image $I_{foc}$, and morphological filters are applied where relevant (step 940). At the end of step 940, a first characteristic image of the sample is obtained, centred on the optical axis, comprising the particle of interest and a plurality of neighbouring particles. This image is stored in a temporary memory.

At a later time, steps 910 to 940 are repeated, having the reference numerals 910' to 940' in the figure, and a second characteristic image of the sample is obtained.

The displacement of the particle of interest between the first and the second moments in time is therefore estimated, in step 950, by comparing the first and second characteristic images.

The first characteristic image forms a control image as described hereinabove.

The estimation of the displacement implements, for example, a cross-correlation calculation, and an alert could be generated if the maximum of the correlation function is less than a predetermined threshold value. Indeed, this can mean that the distribution of the particles in the sample, in the vicinity of the particle of interest, has been significantly disturbed.

In step 960, the sample is translated along a vector proportional to the displacement vector determined in the previous step.

Using a new second characteristic image, it can be checked that the new displacement vector is a zero vector (step 970). Either the previously calculated displacement vector is validated, or an error signal is generated and the operator is asked to select a new particle of interest.

The displacement vector thus validated is used to control the position of the particle of interest and in particular control with feedback its position in the XY plane by controlling the translation stage.

In other words, the invention further includes a method for controlling the position of a particle of interest in an analysis system according to the invention, such that:

at a first moment in time, a first image of the sample is acquired, from which is deduced, by numerical propagation, a first series of reconstructed images of said sample, corresponding to different offset values of the reconstruction plane relative to the image plane, and the image having the greatest contrast is selected from said first series of images as the first characteristic image of the sample;

at a second moment in time, a second image of the sample is acquired, from which is deduced, by numerical propagation, a second series of reconstructed images of said sample, corresponding to different offset values of the reconstruction plane relative to the image plane, and the image having the greatest contrast is selected from said second series of images as the second characteristic image of the sample;

the displacement of the particle of interest between the first and the second moments in time is estimated based on the first and second characteristic images.

The analysis system according to the invention thus includes:

computing means for computing, by numerical propagation, a first (and respectively a second) series of reconstructed images of said sample, corresponding to different offset values of the reconstruction plane relative to the image plane, based on the first (and respectively the second) acquired image;

means for selecting the image having the greatest contrast from the first (and respectively the second) series of reconstructed images as the first (and respectively the second) characteristic image of the sample;

means for estimating the displacement of the particle of interest between the first and the second moments in time based on the first and second characteristic images.

According to a final embodiment, not shown, the step of computing at least one reconstructed image is bypassed.

Indeed, a displacement of a transparent particle can be identified in a simple manner by comparing the defocused image acquired by the image sensor, with a reference image. This comparison can take place using computing means. Alternatively, the image acquired directly by the image sensor is displayed on a screen, so that a user identifies a modification of the image displayed, when the transparent particle is displaced. It can therefore be ensured that a point of interest of the transparent sample is in the correct and expected position, said position being in particular the focusing point of the analysis beam. This verification is preferably implemented after the time period required for the measurement by the analysis device.

This embodiment allows the reconstructed image computation steps to be bypassed. A simple comparison of the defocused images acquired by the image sensor, for example before and after positioning the analysis beam on the point of interest, is used to detect whether the latter has been displaced or damaged by the analysis beam. This constitutes a measurement validity test that is easy to implement, by simply using a detector providing a defocused image of the plane in which is located the focusing point of the analysis beam.

The invention is not limited to the examples disclosed; numerous alternatives can be conceived without leaving the scope of the invention. In particular, the embodiments in FIGS. 2 and 3 can be combined. The analysis system in FIG. 2 can further comprise a support for the sample that can be moved by a manually-operated wheel in order to manually reposition the particle of interest in the target position.

The invention claimed is:

1. A system for analyzing a particle of interest of a biological sample, comprising:
   an analysis pathway, comprising a first light source emitting an analysis light beam, and a first optical system configured to focus the analysis light beam in a plane orthogonal to the optical axis thereof, as a focusing plane;
   a position control pathway, comprising a second light source, an image sensor, and a second optical system at least partially merged with the first optical system such that the first optical system and the second optical system comprise a shared optical system; and
   computing means configured to compute, by numerical propagation, at least one image, reconstructed from an image provided by the image sensor;
   wherein the image sensor is offset relative to an image of the focusing plane by the second optical systems;
   wherein the computing means receives at an input thereto an image provided by the image sensor, and is configured to compute, based on the image provided by the image sensor and by numerical propagation, a series of reconstructed images in reconstruction planes, each of which is offset relative to the plane of the image sensor; and
   wherein the computing means comprises means for determining, based on the series of reconstructed images, an offset relative to the plane of the image sensor, as an optimum offset, associated with a minimum offset between the reconstruction plane and a plane receiving an image of the particle of interest by the second optical system.

2. A system according to claim 1, wherein the computing means receives at an input thereto an image provided by the image sensor, and is configured to compute, based on the image provided by the image sensor and by numerical propagation, a reconstructed image of the particle of interest in the image of the focusing plane.

3. A system according to claim 1, wherein the computing means comprises means for comparing the optimum offset with the distance between the plane of the image sensor and the image of the focusing plane by the second optical system, a result of the comparison determining an axial displacement command, and further comprising displacement means configured to move a support for receiving the sample, in response to the axial displacement command.

4. A system according to claim 1, further comprising partial and/or selective deflection means, to combine the position control pathway and the analysis pathway at an input to the shared optical system.

5. A system according to claim 4, wherein the first light source and the second light source have different wavelengths, and the deflection means is wavelength-selective means.

6. A method for analyzing a particle of interest of a biological sample, implemented within a system according to claim 1, comprising:
   analyzing the particle of interest using the analysis pathway; and
   controlling the position of the particle of interest using the position control pathway;
   wherein implementation of the analyzing and controlling is not separated by an intermediary of moving the sample relative to the analysis and position control pathways;
   wherein the controlling the position comprises:
      acquiring an image of the particle of interest using the image sensor of the position control pathway;
      using the image to construct, by numerical propagation, at least one reconstructed image, in a reconstruction plane that is offset relative to the plane of the image sensor;
   the method further comprising a computing a series of reconstructed images in reconstruction planes, each of which is offset relative to the plane of the image sensor, and selecting the reconstructed image associated with the minimum offset between the corresponding reconstruction plane and a plane receiving the image of the particle by the second optical system.

7. A method according to claim 6, wherein the analyzing and controlling are implemented simultaneously.

8. A method according to claim 6, further comprising computing a reconstructed image of the particle of interest in the image of the focusing plane.

9. A system for analyzing a particle of interest of a biological sample, comprising:
   an analysis pathway, comprising a first light source emitting an analysis light beam, and a first optical system configured to focus the analysis light beam in a plane orthogonal to the optical axis thereof, as a focusing plane;
   a position control pathway, comprising a second light source, an image sensor, and a second optical system at least partially merged with the first optical system such that the first optical system and the second optical system comprise a shared optical system; and
   computing means configured to compute, by numerical propagation, at least one image, reconstructed from an image provided by the image sensor;
   wherein the image sensor is offset relative to an image of the focusing plane by the second optical system;
   wherein the computing means comprises means for comparing a control image with a focused reconstructed image, the focused image being associated with a minimum offset between a position of a corresponding reconstruction plane, and a plane receiving an image of the particle of interest by the second optical system.

10. A system according to claim 9, wherein a result of the comparison between the control image and the focused image determines a transverse displacement command, and further comprising displacement means configured to move a support for receiving the sample, in response to the transverse displacement command.

11. A system for analyzing a particle of interest of a biological sample, comprising:
   an analysis pathway, comprising a first light source emitting an analysis light beam, and a first optical system configured to focus the analysis light beam in a plane orthogonal to the optical axis thereof, as a focusing plane;

a position control pathway, comprising a second light source, an image sensor, and a second optical system at least partially merged with the first optical system such that the first optical system and the second optical system comprise a shared optical system;

computing means configured to compute, by numerical propagation, at least one image, reconstructed from an image provided by the image sensor; and means for thresholding a reconstructed image, the threshold being defined by $i_{th}=i_{av}+3\sigma$ wherein $i_{av}$ is mean value of intensity of the pixels in the reconstructed image and $\sigma$ is standard deviation of the intensity of the pixels in the reconstructed image;

wherein the image sensor is offset relative to an image of the focusing plane by the second optical system.

* * * * *